United States Patent [19]

Robertson et al.

[11] Patent Number: 5,264,445
[45] Date of Patent: Nov. 23, 1993

[54] (−)-N″-CYANO-N-3-PYRIDYL-N′-1,2,2-TRIMETHYLPROPYLGUANIDINE

[75] Inventors: David W. Robertson, Greenwood; Mitchell I. Steinberg, Indianapolis, both of Ind.

[73] Assignee: Eli Lilly and Company, Indianapolis, Ind.

[21] Appl. No.: 968,626

[22] Filed: Oct. 29, 1992

Related U.S. Application Data

[63] Continuation of Ser. No. 306,714, Feb. 3, 1989, abandoned.

[51] Int. Cl.$^5$ .................... C07D 211/02; A61K 31/44
[52] U.S. Cl. ..................................... 514/353; 546/306
[58] Field of Search ......................... 546/306; 514/353

[56] References Cited

U.S. PATENT DOCUMENTS 4,057,636 11/1977 Petersen et al. ................... 424/263

OTHER PUBLICATIONS

FASEB Journal, 3(3), A435 (1989) (Abstract 1214).
Peterson et al., *J. Med. Chem.*, 21 (8), 773 (1978).
Westin et al., *Drugs*, 36 (Supp. 7), 10 (1988).

*Primary Examiner*—C. Warren Ivy
*Assistant Examiner*—Zinna N. Davis
*Attorney, Agent, or Firm*—Robert A. Conrad; Leroy Whitaker

[57] ABSTRACT

This compound provides the compound (−)-N″-cyano-N-3-pyridyl-N′-1,2,2-trimethylpropylguanidine, its salts and pharmaceutical formulations, and its method of use for opening potassium channels in mammals.

3 Claims, No Drawings

(−)-N''-CYANO-N-3-PYRIDYL-N'-1,2,2-TRIMETHYLPROPYLGUANIDINE

This application is a continuation of application Ser. No. 07/306,714, filed Feb. 3, 1989, now abandoned.

BACKGROUND OF THE INVENTION

The field of potassium channels has undergone explosive growth in the past several years. Two events have had a major influence on the rapid growth of this area. First, there has been the development of novel electrophysiological methods including whole cell and patch clamp techniques to characterize potassium channel function at the whole cell and single channel level. Second, there has been the recognition that new classes of pharmacological substances can be developed to specifically block or open such channels. For instance, compounds are available that can specifically block the delayed rectifier channel in cardiac muscle (e.g. clofilium and sotalol) and which now serve as prototypes for an important new class of antiarrhythmic agents, the class III agents. More recently, certain drugs which had previously thought to be "nonspecific vasodilators" (e.g., pinacidil and cromakalim) were found to be selective potassium channel openers (PCO's) in vascular smooth muscle.

It is now known that some 30 different potassium channels exist in a variety of biological tissues. Whereas it has long been known that potassium channels play a major role in neuronal excitability, the recent availability of new probes for K channels has helped reveal the complex and critical role these channels play in the basic electrical and mechanical functions of a wide variety of tissues including smooth and cardiac muscle and glands.

PCO's are derived from a wide variety of structural classes. Pinacidil (N''-cyano-N-4-pyridyl-N'-1,2,2-trimethylpropylguanidine) was derived from a series of alkylpyridylthioureas, which had been demonstrated previously to be direct-acting vasodilators. See U.S. Pat. No. 4,057,636 and Petersen, *J. Med. Chem.*, 21(8), 773 (1982). The cyanoguanidine unit was explored as a bioisosteric replacement for the potentially toxic thiourea moiety, and this resulted in an increase in vasodilator potency. A variety of alkyl groups provided antihypertensive activity, with the best compounds possessing branching at the carbon alpha to the nitrogen. Both 4- and 3-pyridyl isomers were potent vasodilators. The 2-pyridyl isomers were essentially inactive. In Peterson, *J. Med. Chem.*, 21(8), 773 (1982), pinacidil is compound number 50 and the 3-pyridyl isomer is compound number 17. In this report, the minimal effective dose (MED) of pinacidil to decrease blood pressure in spontaneously hypertensive rats was 0.5 mg/kg whereas the MED of the 3-pyridyl isomer was 1 mg/kg.

Pinacidil is currently undergoing clinical trials to determine its antihypertensive potential. By virtue of the branched N-alkyl side chain, pinacidil is a mixture of two enantiomers. Recently, both enantiomers have been prepared and studied -- see, Weston et al., *Drugs,* 36 (Suppl. 7), 10 (1988). It was reported that the (−) isomer of pinacidil was more potent than the (+) isomer.

We have now discovered that the (−) isomer of the 3-pyridyl isomer of pinacidil is considerably more potent as a potassium channel opener as compared with its (+) enantiomer, pinacidil, or any of the pinacidil enantiomers.

SUMMARY OF THE INVENTION

This invention provides the compound (−)-N''-cyano-N-3-pyridyl-N'-1,2,2-trimethylpropylguanidine and its pharmaceutically acceptable acid addition salts thereof.

This invention also provides a method for opening potassium channels in mammals which comprises administering an effective potassium channel opening amount of (−)-N''-cyano-N-3-pyridyl-N'-1,2,2-trimethylpropylguanidine or a pharmaceutically acceptable salt thereof.

This invention also provides for pharmaceutical formulations comprising (−)-N''-cyano-N-3-pyridyl-N'-1,2,2-trimethylpropylguanidine, or a pharmaceutically acceptable salt thereof, together with one or more pharmaceutically acceptable carriers, diluents, or excipients.

PREFERRED EMBODIMENT AND DETAILED DESCRIPTION

When used herein, the compound (−)-N''-cyano-N-3-pyridyl-N'-1,2,2-trimethylpropylguanidine or a pharmaceutically acceptable salt thereof, shall alternately be referred to as "the compound of this invention". While this is the (−)-isomer, alternate nomenclature would regard this compound as the 1-isomer.

This invention includes the pharmaceutically acceptable acid addition salts of (−)-N''-cyano-N-3pyridyl-N'-1,2,2-trimethylpropylguanidine. Since this compound is basic in nature, it can react with any number of inorganic and organic acids to form pharmaceutically acceptable acid additions salts. Acids commonly employed to form such salts include inorganic acids such as hydrochloric, hydrobromic, hydroiodic, sulfuric and phosphoric acid, as well as organic acids such as para-bromophenylsulfonic, carbonic, succinic, citric, benzoic and acetic acid, and related inorganic and organic acids. Such pharmaceutically acceptable salts thus include sulfate, pyrosulfate bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such oxalic acid and maleic acid.

The compound of this invention can be prepared by applying general methods well known in the art, notably U.S. Pat. No. 4,057,636 and Petersen, *J. Med. Chem.*, 21 (8), 773 (1978), which references are specifically incorporated by reference into this specification. (−)-N''-Cyano-N-3-pyridyl-N'-1,2,2-trimethylpropylguanidine can be prepared by resolution of the racemate by classical methods. Such methods include the formation of salts with optically active acids and also by high-pressure liquid chromatography of the racemate over chiral columns.

Alternatively, (−)-N''-cyano-N-3-pyridyl-N'-1,2,2-trimethylpropylguanidine can be made by procedures described in the aforementioned references employing an optically active starting material. Thus, referring to U.S. Pat. No. 4,057,636, cyanamide can be reacted with the appropriate optically active precursor of Formula II to provide the compound of this invention. Alternatively, optically active intermediates III or IV can be reacted with 3-aminopyridine. In like manner, optically active imine V or thiourea VI can be reacted with cyanamide to provide (−)-N''-cyano-N-3-pyridyl-N'-1,2,2-trimethylpropylguanidine. We prefer this latter method, i.e., the reaction of a thiourea of Formula VI with cyanamide to prepare the desired product. The desired thiourea is prepared by the reaction of 3-pyridylisothiocyanate with optically active 2-amino-3,3-dimethylbutane or a salt thereof. This optically active starting material is best prepared by resolving racemic 2-amino-3,3-dimethylbutane by fractional recrystallization of the desired optically active tartaric acid salt. For example, to prepare the optically active amine intermediate for preparing the compound of this invention, L(+)-tartaric acid is employed. The reaction of 3-pyridylisothiocyanate and optically active (−)-2-amino-3,3-dimethylbutane L(+)-tartrate is best accomplished by mixing approximately equal molar amounts of the two reagents in a nonreactive solvent, such as tetrahydrofuran, in the presence of a nonreactive acid scavenger, such as a trialkylamine or pyridine. This reaction is performed at temperatures from about 25° C. up to the reflux temperature of the reaction mixture. When heated at reflux, the transformation to the desired thiourea is usually complete in approximately 18 hours.

The resulting (−)-N-3-pyridinyl-N'-(1,2,2trimethylpropyl) thiourea is then transformed into (−)-N''-cyano-N-3-pyridyl-N'-1,2,2-trimethylpropylguanidine by treating the thiourea with a carbodiimide reagent, such as 1,3-dicyclohexylcarbodiimide, and cyanamide in a nonreactive solvent such as acetonitrile. In addition, it is preferred that a nonreactive acid scavenger, such as a trialkylamine, also be employed. Generally, slight molar excesses of the carbodiimide and cyanamide reagents are employed relative to the thiourea starting material The reaction is generally accomplished at temperatures from about 0°-50° C. and the reaction is essentially complete when stirred at approximately 25° C. for about 18 hours.

The following example illustrates the preparation of the compound of this invention. This method is illustrative of only and is not intended to limit the scope of this invention in any respect and should not be so construed.

EXAMPLE 1

(−)-N''-Cyano-N-3-pyridyl-N'-1,2,2-trimethylpropylguanidine

A. Preparation of (−)-N-3-pyridinyl-N'-(1,2,2-trimethylpropyl)thiourea.

To a slurry of 9.2 g of (−)-2-amino-3,3dimethylbutane, L(+)-tartrate in approximately 100 ml of tetrahydrofuran under a nitrogen atmosphere were added 21 ml of triethylamine. After stirring for 15 minutes, 5 g of 3-pyridylisothiocyanate were added with stirring. The solution was heated at reflux overnight, then cooled and concentrated in vacuo. The resulting oil was purified by high-pressure chromatography over silica gel. The appropriate fractions were combined and concentrated in vacuo to provide 9 g of the desired title intermediate as a thick oil.

Analysis for $C_{12}H_{19}N_3S$
Calc.: C, 60.72; H, 8.07; N, 17.70;
Found C, 59.93; H, 7.99; N, 16.34.

B. Preparation of (−)-N''-cyano-N-3-pyridyl-N'-1,2,2-trimethylpropylguanidine.

Three grams of the thiourea from Example 1A above, 3.9 g of 1,3-dicyclohexylcarbodiimide, and 1.06 g of cyanamide were added to approximately 50 ml of acetonitrile under a nitrogen atmosphere. Five drops of N,N-diisopropylethylamine were added and the mixture was stirred at room temperature overnight. The mixture was then concentrated in vacuo and the resulting paste was triturated with 100 ml of 4:1 hexane/diethyl ether. The liquid was decanted and the residual solid was stirred in 100 ml of 0.8 N hydrochloric acid for 1 hour. The solution was filtered and the filtrate was adjusted to pH 8. The resulting solid was recovered by filtration and crystallized from methanol/water to provide 1.3 g of the desired title product, m.p. 144–145° C. The optical rotation in methanol: $[\alpha]_D = -165.365°$.

Analysis for $C_{13}H_{19}N_5$:
Calc.: C, 63.65; H, 7.81; N, 28.55;
Found C, 63.88; H, 7.84; N, 28.69

In the same way was prepared (+)-N''-cyano-N-3-pyridyl-N'-1,2,2-trimethylpropylguanidine, m.p. 141–142° C. $[\alpha]_D = +161.034°$ in methanol.

Analysis for $C_{13}H_{19}N_5$
Calc.: C, 63.65; H, 7.81; N, 28.55;
Found: C, 63.39; H, 7.99; N, 28.35.

The compound of this invention is a potassium channel agonist or "opener". As such, the compound causes vasodilation, making it an effective antihypertension agent, and will be useful for treating other related conditions and disease states, such as asthma, interstitial cystitis, urinary incontinence and other urogenital disorders, ischemic bowel disease, gastrointestinal motility disorders, arrhythmias, peripheral vascular disease, dysmenorrhea, glaucoma, angina, and alopecia. Depending upon the particular condition or disease to be treated, the compound of this invention is administered alone or in combination with one or more other pharmacologically active agents but in a form substantially free of (+)-N''-cyano-N-3-pyridyl-N'-1,2,2-trimethylpropylguanidine.

The ability for (−)-N''-cyano-N-3-pyridyl-N'-1,2,2-trimethylpropylguanidine to affect cardiac electrophysiological and vasorelaxant parameters was demonstrated in canine tissues in vitro as compared with its (+)-isomer, racemic N''-cyano-N-3-pyridyl-N'-1,2,2-trimethylpropylguanidine, and the racemate and individual enantiomers of pinacidil. All six compounds were tested in the Purkinje fiber and canine cephalic vein assays taught by Steinberg et al., *Journal of Cardiovascular Pharmacology*, 12 (Suppl. 2), S30–S40 (1988). The effective concentration for reducing the Purkinje fiber action potential duration and for relaxing phenylephrine-contracted cephalic veins, respectively, otherwise known as the $EC_{50}$, was determined for each compound and is reported in Table I.

TABLE I

| | $EC_{50}$ (μM)* | |
|---|---|---|
| Compound | Canine Cephalic Vein | Purkinje Fiber |
| (±)-Pinacidil | 0.76 ± 0.12 | 3.0 ± 1.0 |
| (−)-Pinacidil | 0.44 ± 0.10 | 3.2 ± 1.2 |
| (+)-Pinacidil | 9.55 ± 0.07 | 55 ± 9.6 |
| (±)-N''-cyano-N-3- | 0.56 ± 0.14 | 0.50 ± 0.03 |

TABLE I-continued

| Compound | EC$_{50}$ ($\mu$M)* | |
|---|---|---|
| | Canine Cephalic Vein | Purkinje Fiber |
| pyridyl-N'-1,2,2-trimethylpropyl guanidine | | |
| (−)-N''-cyano-N-3-pyridyl-N'-1,2,2-trimethylpropyl guanidine | 0.09 ± 0.03 | 0.43 ± 0.26 |
| (+)-N''-cyano-N-3-pyridyl-N'-1,2,2-trimethylpropyl-guanidine | 6.41 ± 1.8 | 23 ± 4.7 |

*±SEM

The compound of this invention and its pharmaceutically acceptable salts are preferably formulated prior to administration. Therefore, yet another embodiment of the present invention is a pharmaceutical formulation comprising (−)-N''-cyano-N-3-pyridyl-N'-1,2,2-trimethylpropylguanidine, or a pharmaceutically acceptable salt thereof, and one or more pharmaceutically acceptable carriers, diluents or excipients. The formulation may contain the compound of this invention as the single bioactive agent or in combination with one or more other pharmacologically active drugs in a form substantially free of (+)-N''-cyano-N-3-pyridyl-N'-1,2,2-trimethylpropylguanidine.

The present pharmaceutical formulations are prepared by known procedures using well known and readily available ingredients. In making the compositions of the present invention, the active ingredient(s) will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders. The active component typically accounts for about 1% to about 95% of the formulation by weight.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl-and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

Dosages of from about 0.5 to about 300 mg/kg per day, preferably 0.5 to 20 mg/kg, of the compound of this invention may be administered although it will, of course, readily be understood that the amount of (−)-N''-cyano-N-3-pyridyl-N'-1,2,2-trimethylpropylguanidine actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The following formulation examples are illustrative only and are not intended to limit the scope of the invention in any way.

Formulation 1

Hard gelatin capsules are prepared using the following ingredients:

| | Quantity (mg/capsule) |
|---|---|
| (−)-N''-cyano-N-3-pyridyl-N'-1,2,2-trimethylpropylguanidine hydrochloride | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

| | Quantity (mg/tablet) |
|---|---|
| (−)-N''-cyano-N-3-pyridyl-N'-1,2,2-trimethylpropylguanidine | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

| | Weight % |
|---|---|
| (−)-N''-cyano-N-3-pyridyl-N'-1,2,2-trimethylpropylguanidine sulfate | 0.25 |
| ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| | |
|---|---|
| (−)-N''-cyano-N-3-pyridyl-N'-1,2,2-trimethylpropylguanidine napsylate | 60 mg |
| starch | 45 mg |
| microcrystalline cellulose | 35 mg |
| polyvinylpyrrolidone (as 10 solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| | |
|---|---|
| (−)-N''-cyano-N-3-pyridyl-N'-1,2,2-trimethylpropylguanidine | 80 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg. of active ingredient may be made as follows:

| | |
|---|---|
| (−)-N''-cyano-N-3-pyridyl-N'-1,2,2-trimethylpropylguanidine | 225 mg |
| saturated fatty acid glycerides | 2,000 mg |
| Total | 2,225 mg |

The active ingredient is passed through a No. 60 mesh U.S. sieve and suspended din the saturated fatty acid glycerides previously melted using the minimum heat necessary. The mixture is then poured into a suppository mold of nominal 2 g capacity and allowed to cool.

Formulation 7

Suspensions each containing 50 mg. of medicament per 5 ml dose are made as follows:

| | |
|---|---|
| (−)-N''-cyano-N-3-pyridyl-N'-1,2,2-trimethylpropylguanidine | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | |
|---|---|
| (−)-N''-cyano-N-3-pyridyl-N'-1,2,2-trimethylpropylguanidine hydrochloride | 100 mg |
| isotonic saline | 1000 ml |

The solution of the above ingredients is administered intravenously at a rate of 1 ml per minute to a subject in need of treatment.

We claim:

1. (−)-N''-Cyano-N-3-pyridyl-N'-1,2,2-trimethylpropylguanidine and pharmaceutically acceptable addition salts thereof.

2. (−)-N''-Cyano-N-3-pyridyl-N'-1,2,2-trimethylpropylguanidine.

3. A pharmaceutical composition comprising a compound of claim 1 and one or more pharmaceutically acceptable carriers, diluents, or excipients.

* * * * *

UNITED STATES PATENT AND TRADEMARK OFFICE
CERTIFICATE OF CORRECTION

Page 1 of 2

PATENT NO.    :    5,264,445

DATED    :    November 23, 1993

INVENTOR(S)    :    David W. Robertson, et al.

It is certified that an error appears in the above-identified patent and that said Letters Patent is hereby corrected as shown below:

Title page, item [57], line 1,
In the abstract, delete "This compound provides", and insert therefor --This invention provides--.

Column 2, line 26, delete "1", and insert therefor --*1*--.

Column 2, line 28, delete "N-3pyridyl", and insert therefor --N-3-pyridyl--.

Column 2, line 53, delete "lene-1sulfonate,", and insert therefor --lene-1-sulfonate,--.

Column 3, line 34, delete "(1,2,2trimethyl", and insert therefor --(1,2,2-trimethyl--.

Column 3, line 44, delete "material", and insert therefor --material.--.

Column 3, line 58, delete "3,3dimethylbu-", and insert therefor --3,3-dimethylbu--.

UNITED STATES PATENT AND TRADEMARK OFFICE
CERTIFICATE OF CORRECTION

PATENT NO. : 5,264,445

DATED : November 23, 1993

INVENTOR(S) : David W. Robertson, et al.

It is certified that an error appears in the above-identified patent and that said Letters Patent is hereby corrected as shown below:

Column 3, line 64, delete "in vacuo", and insert therefor --in vacuo--.

Column 3, lines 66 and 67, delete "in vacuo", and insert therefor --in vacuo--.

Column 4, line 12, delete "in vacuo", and insert therefor --in vacuo--.

Column 4, line 48, delete "in vitro", and insert therefor --in vitro--.

Column 7, line 15, delete "10 solution", and insert therefor --10% solution--.

Column 8, line 9, delete "din", and insert therefor --in--.

Signed and Sealed this

Twenty-second Day of November, 1994

Attest:

BRUCE LEHMAN

*Attesting Officer*          *Commissioner of Patents and Trademarks*